United States Patent
Holtz et al.

(10) Patent No.: US 10,773,001 B2
(45) Date of Patent: Sep. 15, 2020

(54) MEDIA SEPARATION DEVICE

(71) Applicant: MEDELA HOLDING AG, Baar (CH)

(72) Inventors: Raymond Holtz, Chicago, IL (US); David Y. Cho, Arlington Heights, IL (US); Kathryn Mizuchi, Round Lake Beach, IL (US)

(73) Assignee: MEDELA HOLDING AG, Baar (CH)

( * ) Notice: Subject to any disclaimer, the term of this patent is extended or adjusted under 35 U.S.C. 154(b) by 444 days.

(21) Appl. No.: 15/040,253

(22) Filed: Feb. 10, 2016

(65) Prior Publication Data
US 2016/0228624 A1    Aug. 11, 2016

Related U.S. Application Data

(60) Provisional application No. 62/114,476, filed on Feb. 10, 2015.

(51) Int. Cl.
*A61M 1/06* (2006.01)
*B01D 19/00* (2006.01)

(52) U.S. Cl.
CPC .............. *A61M 1/06* (2013.01); *A61M 1/066* (2014.02); *B01D 19/0031* (2013.01); *A61M 2207/00* (2013.01)

(58) Field of Classification Search
CPC combination set(s) only.
See application file for complete search history.

(56) References Cited

U.S. PATENT DOCUMENTS

| | | | |
|---|---|---|---|
| 4,668,459 A | 5/1987 | Joh | |
| 2004/0039330 A1* | 2/2004 | Silver | A61M 1/06 604/74 |
| 2004/0087898 A1 | 5/2004 | Weniger | |
| 2007/0191763 A1* | 8/2007 | Nueesch | A61M 1/06 604/74 |
| 2008/0171970 A1* | 7/2008 | Luzbetak | A61M 1/0049 604/74 |
| 2009/0254029 A1* | 10/2009 | Tashiro | A61M 1/06 604/74 |

(Continued)

FOREIGN PATENT DOCUMENTS

| | | |
|---|---|---|
| EP | 2609942 A1 | 7/2013 |
| WO | WO-99/51882 A1 | 10/1999 |

(Continued)

OTHER PUBLICATIONS

International Search Report and Written Opinion, International application No. PCT/IB2016/000214, dated Jun. 1, 2016.

(Continued)

*Primary Examiner* — Jonathan M Peo
(74) *Attorney, Agent, or Firm* — Marshall, Gerstein & Borun LLP

(57) ABSTRACT

A directed media separation system includes components for directing a consistent collapse of a media separation device in response to a varying pressure from a pressure source. The media separation device can be removably connected to a directing element. The directing element can have a directing geometry that affects the collapse of the media separation device. The media separation device can have a preset geometry that collapses in a predictable and repeatable manner from the applied pressure.

30 Claims, 11 Drawing Sheets

(56) References Cited

U.S. PATENT DOCUMENTS

2014/0094748 A1* 4/2014 Hong .................. A61M 1/06
 604/74
2016/0082166 A1 3/2016 Guthrie et al.

FOREIGN PATENT DOCUMENTS

WO  WO-2008/057218 A2   5/2008
WO  WO-2014045159 A1 *  3/2014  .............. A61M 1/06

OTHER PUBLICATIONS

European Patent Application No. 16710488.4, Communication Pursuant to Article 94(3) EPC, dated Jan. 2, 2019.
Chinese Patent Application No. 201680012605.X, First Office Action, dated Sep. 30, 2019.
Chinese Patent Application No. 201680012605.X, Second Office Action, dated May 28, 2020.

* cited by examiner

MEDIA SEPARATION DEVICE

CROSS-REFERENCE TO RELATED APPLICATION

This application claims the benefit of the filing date of U.S. Provisional Patent Application No. 62/114,476, filed Feb. 10, 2015. U.S. Provisional Patent Application No. 62/114,476 is hereby incorporated by reference.

FIELD OF THE DISCLOSURE

The present disclosure relates to a directed media separation (DMS) system for use in a pressure system, such as a breastmilk expression system, to maintain separation of a primary media system from a secondary media system, where the secondary media system is configured to move liquid through the system.

BACKGROUND

A media separation device can be used in a pressure generating system to separate one medium from another medium, particularly in applications where it is important to separate various media, such as liquid/liquid separation, gas/liquid separation, or a combination of gas/liquid on one or both sides of the media separation device. One example of a combination of media is a combination of breastmilk and humidified air. The media separation device can be used in a breast pump system to maintain separation of a media pathway from breast milk passing from a breastshield to a container of the system. However, certain inefficiencies can arise from the use of known media separation devices, such as unpredictable deformation of the media separation device produced in response to an applied pressure.

The unpredictable deformation that can arise in known media separation devices can add noise to the system. Any extra noise in the system can distract the mother, and/or can reduce the mother's discretion during the mother's pumping session.

Another problem that can be associated with the unpredictable deformation of known media separation devices is the energy necessary to achieve the deformed state and to return the devices to the undeformed state. The amount of energy to cause the deformed state of known devices can vary, so known systems must be designed to accommodate the maximum possible amount of energy required to reach the deformed state. Further, the variable nature of the energy amount caused by known media separation devices may contribute to uneven pressure pattern delivery, and/or unnecessary wear on the pump motor.

Thus, there is an existing need for a media separation device that overcomes the inefficiencies and problems of known devices.

SUMMARY OF THE DISCLOSURE

The present disclosure relates to a predictable and repeatable directed media separation (DMS) system that can provide added comfort for the user in a pressure generating system, such as a breastmilk expression system. One example of a suitable pressure generating system is a vacuum system. Components of the DMS system are formed so that a media separation system of the breastmilk expression system will collapse in a predictable and repeatable manner.

In an exemplary embodiment, the DMS system includes a media separation device and a directing element. The media separation device is operably and removably connected to, or otherwise disposed on, the directing element. The media separation device advantageously has a preset, or selected, geometry that affects a collapse of the device from a directing geometry of the directing element when subjected to a given pressure from a pressure source, where the collapse of the media separation device is predictable and repeatable. More specifically, the collapse of the media separation device is predictable and repeatable relative to the directing element when a varying pressure is applied to the device.

In an embodiment, the media separation device is formed of a suitable flexible material, and if desired, can be capable of reverting to the preset geometry upon removing the pressure. The media separation device may include an elongate sleeve defined by a continuous wall to have an open end, a closed end, front and back wall portions, and opposed side wall portions, and it may include one or more outwardly projecting rims. More specifically, the outwardly projecting rims may be provided generally where the open end of the elongate sleeve engages the directing element.

The media separation device can include at least one first wall region having a first pressure response and at least one second wall region having a second pressure response. The first pressure response of the first wall region(s) can differ from the second pressure response of the second wall region(s) when the given pressure is applied to both the first and second wall region(s), so that breastmilk can flow past the media separation device to the container for certain exemplary configurations.

In an exemplary embodiment, the front and back wall portions and opposed side wall portions each include a first wall region of a first thickness extending from the open end toward the closed end of the elongate sleeve. The front and back wall portions also each include a second wall region of a second thickness extending from the closed end toward the open end of the elongate sleeve. With regard to the remaining wall region of the media separation device, it has a third thickness which is less than the first thickness of the first wall region and greater than the second thickness of the second wall region.

In one embodiment, the first thickness of the first wall region of each of the opposed side wall portions is chevron-shaped, the first wall region of the front and back wall portions is rectangular, and the second thickness of the second wall region of each of the front and back wall portions is inverted U-shaped and extends about the closed end.

In another embodiment, the continuous wall defining the elongate sleeve includes an outer surface and an inner surface defining a fluid (or other media) cavity, configured to selectively collapse when a varying pressure is applied. The first wall region includes a projection of the inner surface of the continuous wall into the fluid cavity, whereas the second wall region includes a recess in the outer surface of the continuous wall.

In an exemplary embodiment, the directing element projects downwardly, or takes any suitable geometry for directing the media separation device to collapse in an efficient manner, rather than deform, within a breastmilk expression system. Advantageously, an exterior of the media separation device can be movably positioned and in media communication with a media pathway of the secondary media system, or secondary pathway, that extends from a breastshield to a container, where such placement improves the efficiency of the system. An interior of the media separation device is in media communication with a media pathway of the primary media system, or primary pathway, which includes a pressure source, which in various embodiments is a vacuum source. The pressure source in the primary pathway applies varying pressure to the media separation device.

In one embodiment, the elongate sleeve has an oval-shaped axial cross-section substantially from the open end to the closed end. The directing element has an oval-shaped axial cross-section, and a downwardly facing angled surface extending through a major axis of the oval-shaped cross-section. Additionally, the directing element has a channel for media communication of the interior of the media separation device with the pressure source.

With this arrangement, the downwardly facing surface of the directing element slants away from the media pathway from the breastshield toward an end of the container, and the cap has a media passageway extending from a port, in media communication with the primary pathway of the pressure source, to the channel of the directing element to apply a pressure to the media separation device.

In another embodiment, a conduit system has multiple interfaces. The conduit system includes distinct interfaces for receiving one or more of a breastshield, a cap having the directing element projecting downwardly from its underside, and a container. The conduit system has a media separation well configured to receive the media separation device and, if desired, the directing element.

The media separation well of the conduit system, the media separation device, and the directing element can all have an oval-shaped cross-section, if desired, whereby the media separation device can be disposed on the directing element and the media separation device can be disposed in the media separation well of the conduit system.

In an exemplary embodiment, the media separation device is disposed within a primary pathway, and includes a first noise attenuation region, disposed nearer and in communication with the secondary media path, and a second noise attenuation region, disposed further from a terminal end of a nipple tunnel in the secondary media path than the first noise attenuation region.

The first noise attenuation region includes one wall region having a first thickness configured to generate a first pressure response and the second noise attenuation region includes another wall region having a second thickness configured to generate a second pressure response. Further, the first pressure response of the first wall region can differ from the second pressure response of the second wall region for a varying pressure which is applied to both of the wall regions by the pressure source via the primary pathway.

Other advantages and features of the disclosure will become apparent from a consideration of the following specification when taken in conjunction with the accompanying drawings.

DETAILED DESCRIPTION OF THE PREFERRED EMBODIMENTS

Figure 1:
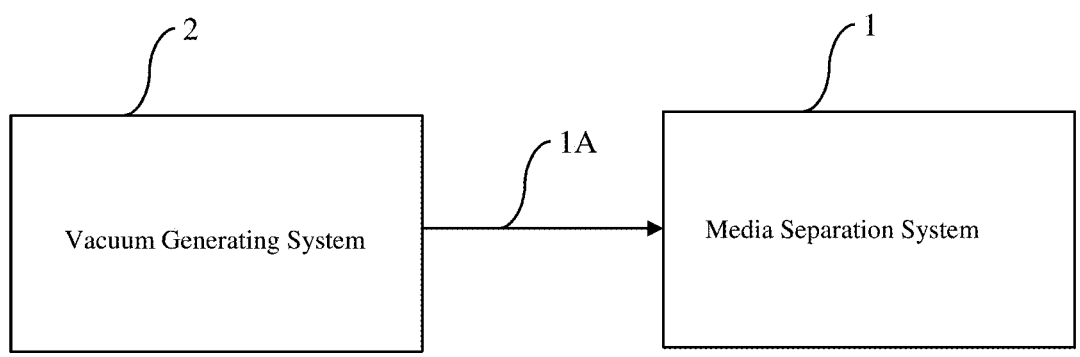
FIG. 1 is a block diagram of a pressure generating system, or pressure source, acting on a media separation system via a tubing system in accordance with the present disclosure.

Referring to the drawings, and first to FIG. 1, the present disclosure is generally directed to a directed media separation (DMS) system 1 for a pressure generating system, or pressure source 2, such as a breastmilk expression system, where a media separation device of the DMS is formed to collapse in a predictable and repeatable manner. The media separation device is exposed to a varying pressure applied from the pressure source 2 via a primary pathway formed by a suitable connection, such as a tubing system 1A connecting the pressure source 2 to a breastshield assembly and DMS 1. Unlike known devices, a system constructed in accordance with the principles of the present disclosure does not merely deform in response to an applied pressure, but instead undergoes an efficient and repeatable collapse due to the overall configuration of the components of the directed media separation system.

Figure 2A:
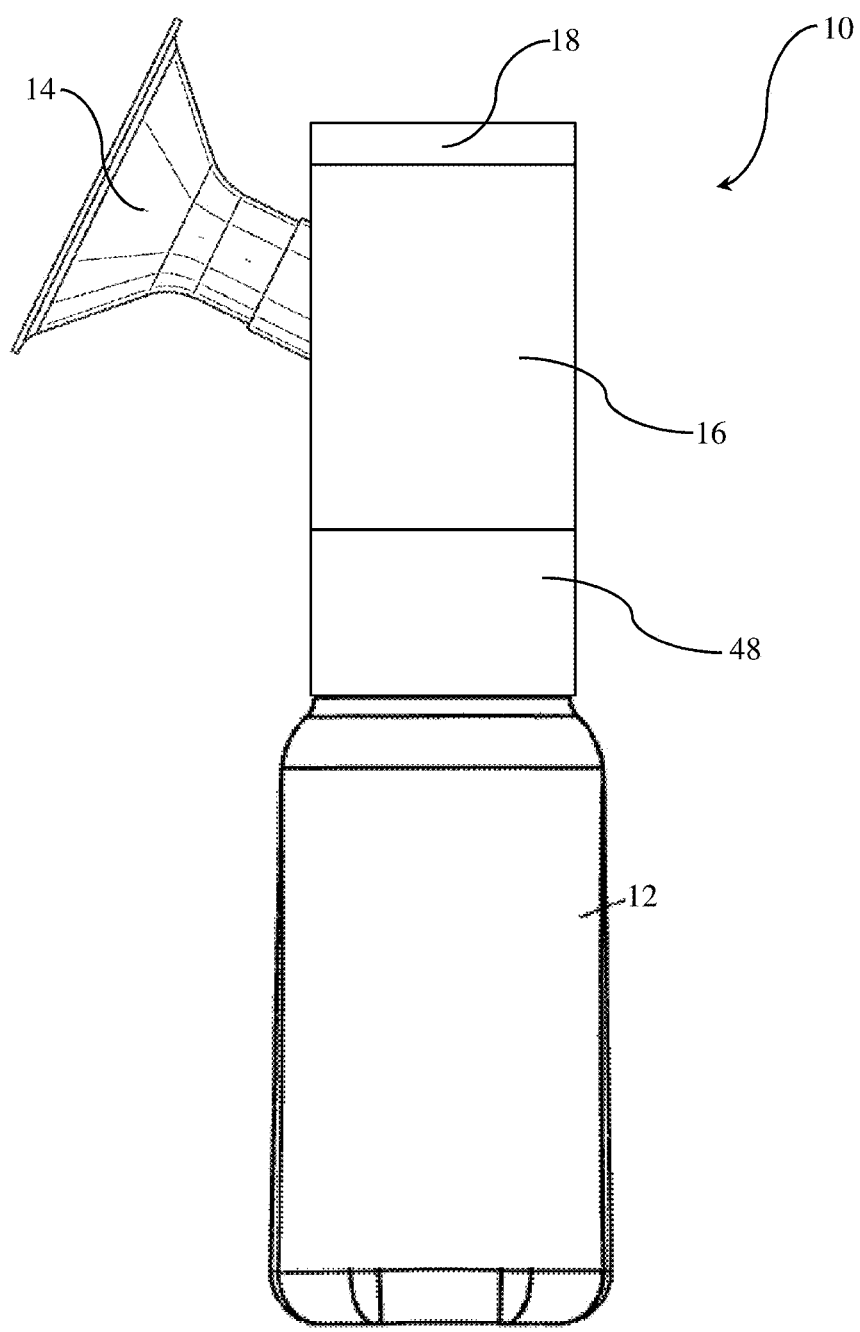
FIG. 2A is a first perspective view of a breastshield assembly for use as part of a pressure generating system, such as a breastpump.
Figure 2B:
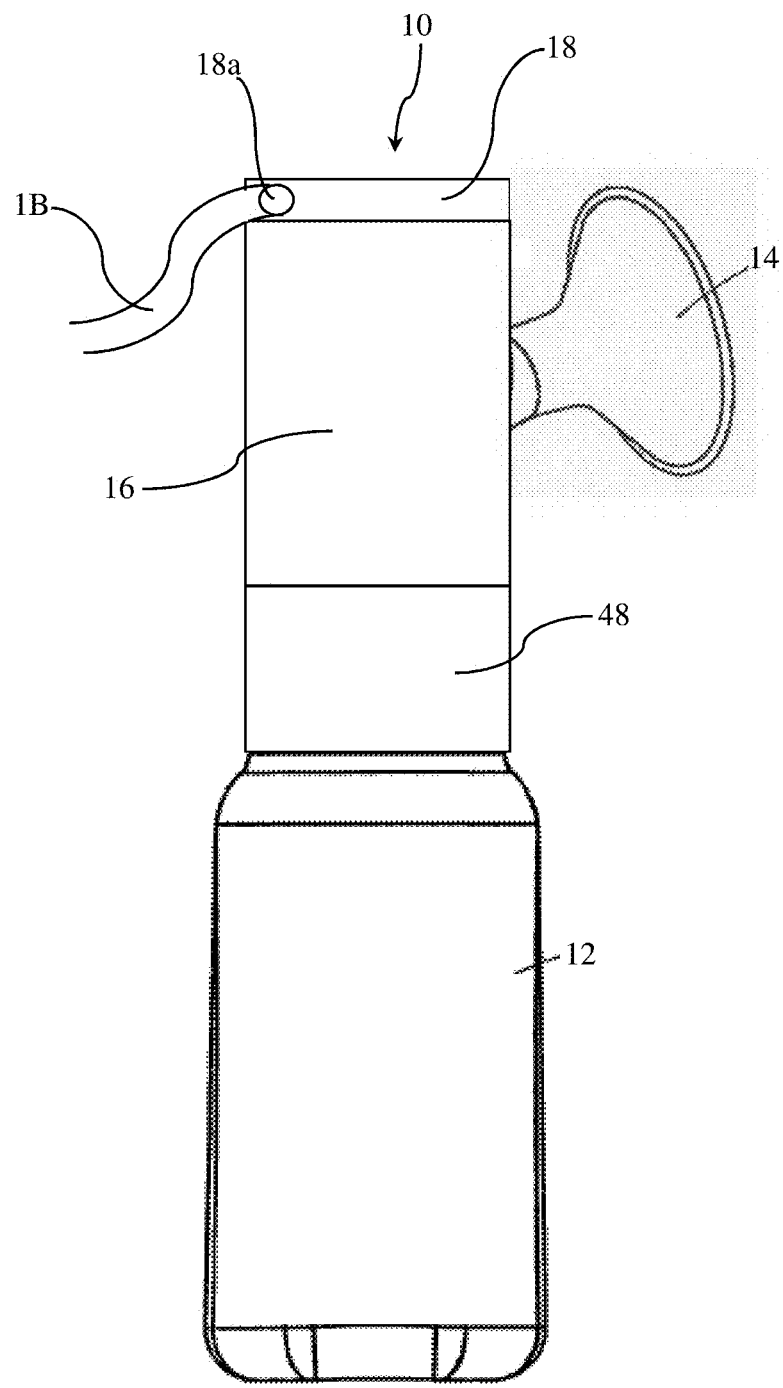
FIG. 2B is a second perspective view of a breastshield assembly for use as part of a pressure generating system, such as a breastpump.

Referring to FIGS. 2A and 2B, the reference numeral 10 designates generally one embodiment of a suitable exemplary breastshield assembly for use in a pressure system, such as a breastmilk expression system. The assembly 10 can include a breastshield 14, a conduit system 16, configured to selectively attach to a container 12, and a cap 18. The term breastmilk expression system, as used herein, refers to any system designed to express breastmilk that can benefit from including a media separation system therein, where the media separation system is constructed in accordance with the principles of the present disclosure, and where the media separation system is used in association with components of the breastmilk expression system.

Figure 3:
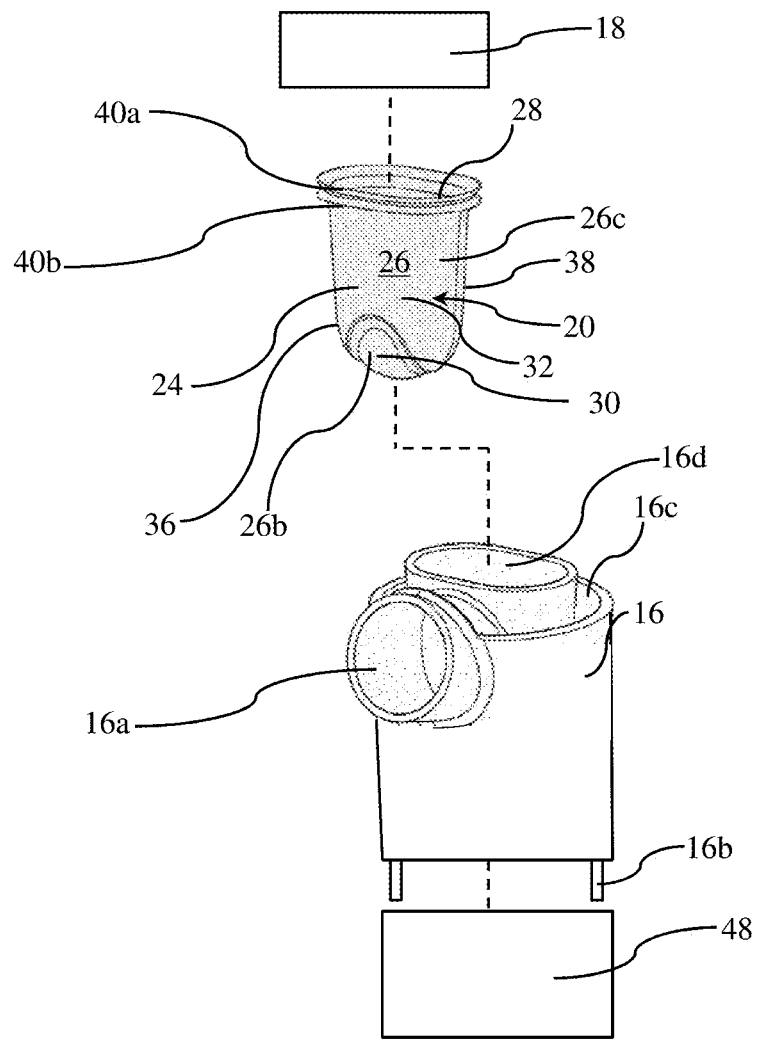
FIG. 3 is an exploded perspective view of the components of the breastshield assembly of FIGS. 2A and 2B, except for a shield.
Figure 5:
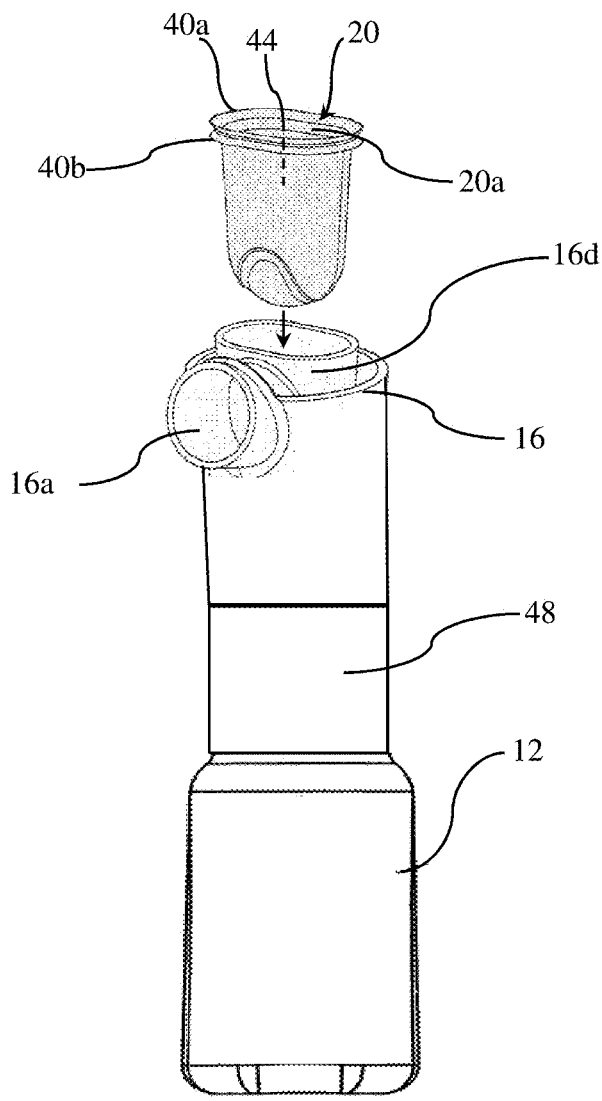
FIG. 5 is a perspective view of the breastshield assembly of FIGS. 2A and 2B with the cap removed illustrating placement of a media separation device.
Figure 5A:
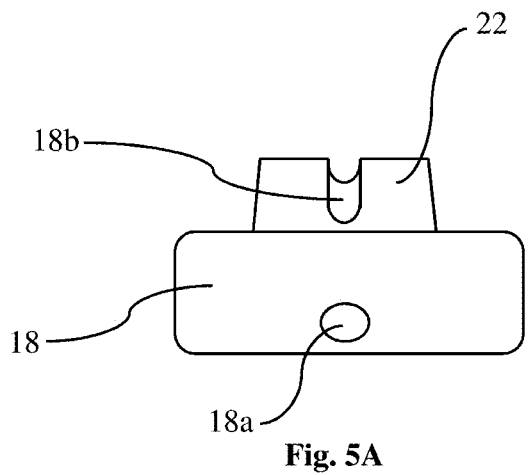
FIG. 5A is a perspective view of the cap of FIG. 3 illustrating a media path extending through the cap.
Figure 5B:
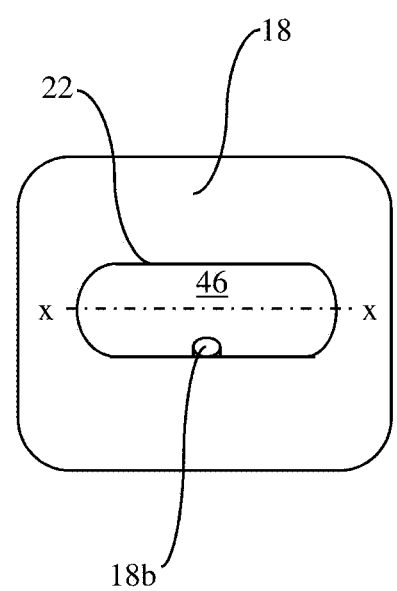
FIG. 5B is a perspective view of a cap similar to FIG. 5A illustrating a projection extending downwardly to receive a media separation device.

A media separation device 20, as illustrated in the exploded perspective view of an exemplary embodiment illustrated in FIG. 3, is adapted and configured to be operably and removably connected to, or otherwise disposed on, a directing element 22, illustrated in FIG. 5A and discussed below. The directing element 22 can be formed in a suitable location upstream of the pressure generating source, for example, on the underside of the cap 18 as shown in FIGS. 5A and 5B, or any other suitable location. The media separation device 20 is configured to have a preset geometry that affects a selective collapse from the preset geometry in a predictable and repeatable manner relative to the directing element 22.

More specifically, the cushioning media separation device 20 undergoes a "directed collapse", that is predictable and repeatable relative to the directing element 22, unlike known devices which merely deform, when a varying pressure is applied to the device 20 in a manner that will be described in greater detail below.

The media separation device 20 can be formed of a suitable material, such as a flexible material that can be capable of reverting to the preset geometry upon removing the pressure, if desired. Said another way, the media separation device 20 may be formed of any material capable of reverting to the preset geometry upon removal of the pressure, such as one or more of an elastic, pliable, supple, bendable, stretchy, springy or resilient material. Still further, such material is capable of bending easily without breaking, for example, and independently, e.g., automatically, returning to its original, preset geometry, e.g., a preset configuration, form, or configuration. In one example, the suitable material may include any type of plastic, rubber, or a combination of plastic and rubber, for example, or any other material having the material properties that allow the material separation device 20 to revert to the preset, original geometry. Further, the suitable material can include, at least in part, a flexible material capable of selectively collapsing predictably and repeatedly under a varying pressure and capable of reverting to a preset geometry upon removal of the varying pressure, rather than just deforming randomly in response to an applied pressure, for example.

The device 20 may include an elongate sleeve 24 (see, e.g., FIGS. 6A-6C) defined by a continuous wall 26 to have an open end 28, a closed end 30, front and back wall portions 32 and 34, and opposed side wall portions 36 and 38. In addition, the device 20 may include one or more outwardly projecting rims 40a and 40b (see FIG. 3), and the outwardly projecting rims 40a and 40b may be provided generally where the open end 28 of the elongate sleeve 24 receives the directing element 22.

Figure 6A:
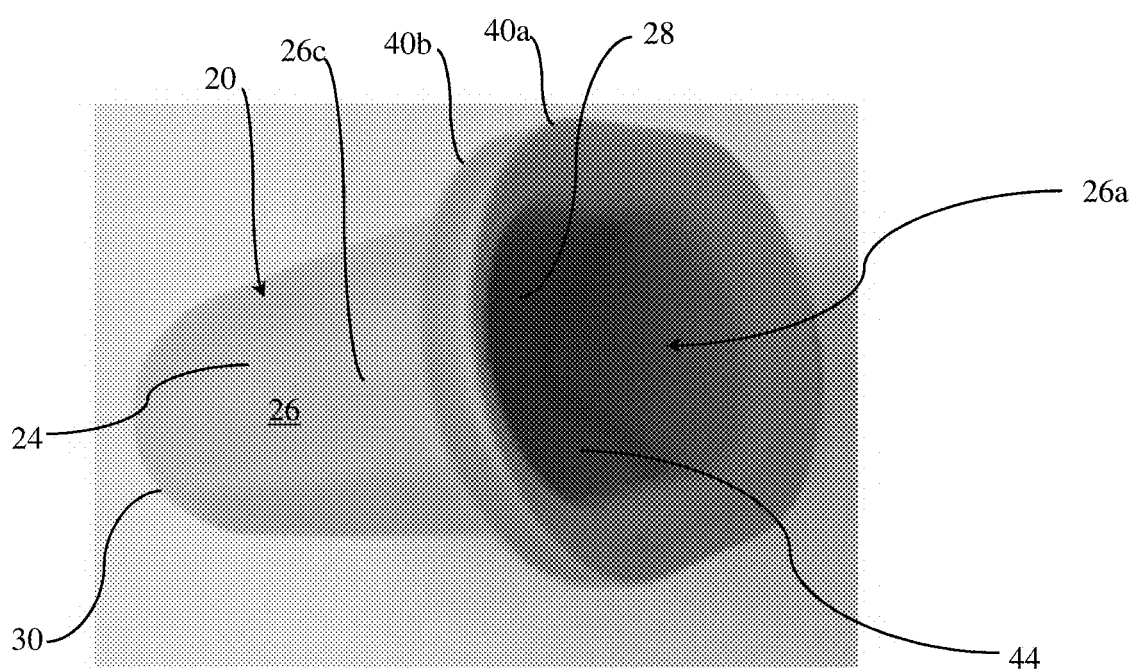
FIG. 6A is a perspective view of a media separation device such as the one in FIG. 5 illustrating a first interior feature.
Figure 6B:
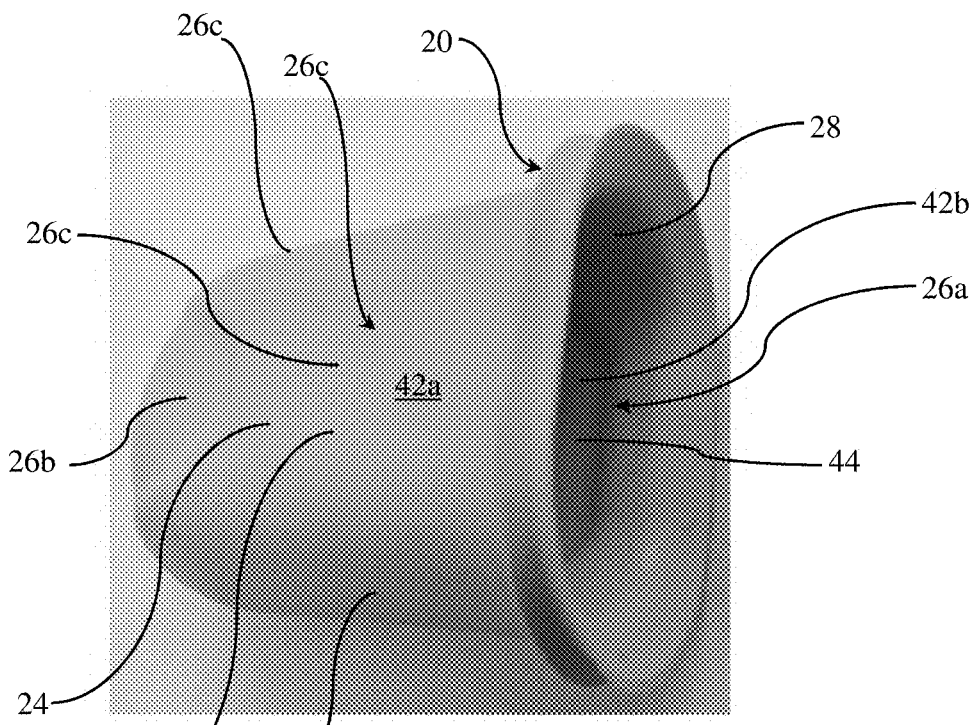
FIG. 6B is a perspective view of a media separation device such as the one in FIG. 5 illustrating a second interior feature.
Figure 6C:
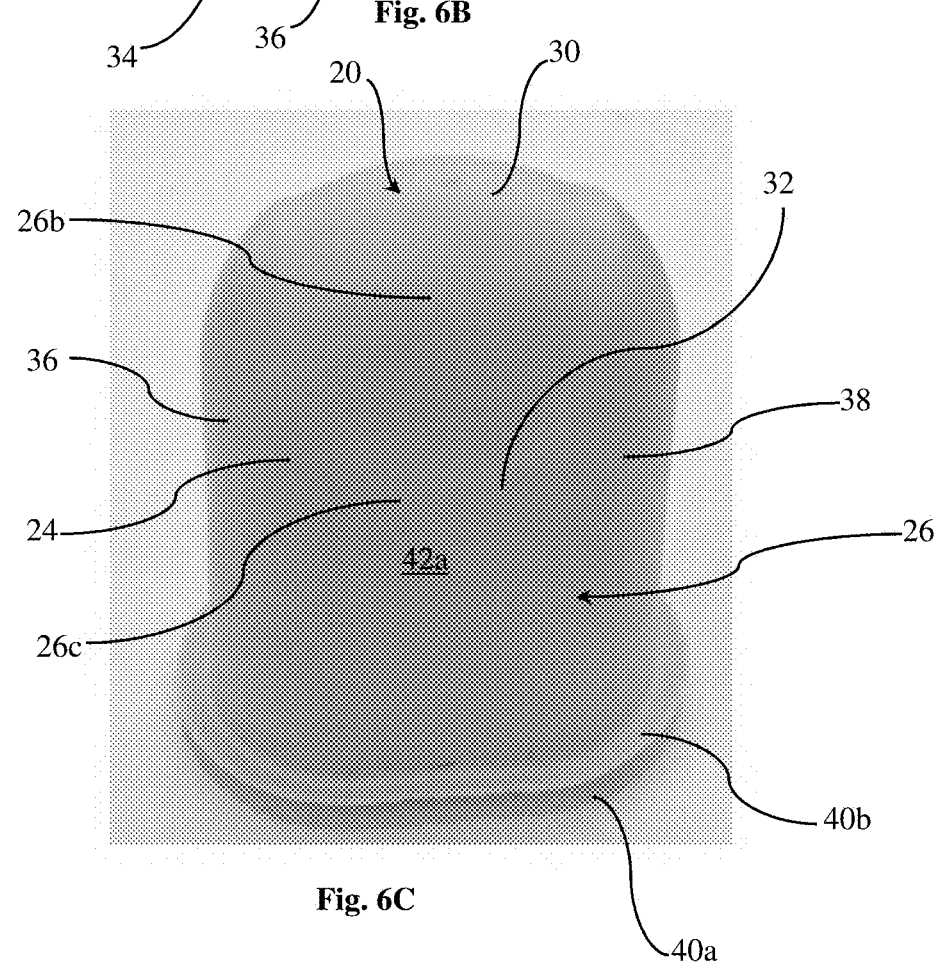
FIG. 6C is a perspective view of a media separation device such as the one in FIG. 5 illustrating an exterior feature.

Referring to FIGS. 6A-6C, the front and back wall portions 32 and 34 and opposed side wall portions 36 and 38 each can include a first wall region 26a having a first thickness and extending from the open end 28 toward the closed end 30 of the elongate sleeve 24. The front and back wall portions 32 and 34 also each can include a second wall region 26b having a second thickness and extending from the closed end 30 toward the open end 28 of the elongate sleeve 24. A remaining wall region 26c can be formed to have a third thickness which is at least one of less than the first thickness of the first wall region 26a and greater than the second thickness of the second wall region 26b.

As best illustrated in exemplary embodiments shown in FIGS. 6A-6C, the first thickness of the first wall region 26a of each of the opposed side wall portions 36 and 38 can be chevron-shaped (see FIG. 6A), the first wall region 26a of the front and back wall portions 32 and 34 can be rectangular (see FIG. 6B), and the second thickness of the second wall region 26b of each of the front and back wall portions 32 and 34 can be inverted U-shaped and extends about the closed end 30 (see FIG. 6C).

The continuous wall 26 defining the elongate sleeve 24 can include an outer surface 42a and an inner surface 42b defining a fluid cavity 44 configured to selectively collapse when a varying pressure is applied to the fluid cavity 44. FIGS. 6A-6C illustrate the first wall region 26a that can include a projection of the inner surface 42b of the continuous wall 26 into the fluid cavity 44 and the second wall region 26b can include a recess in the outer surface 42a of the continuous wall 26.

Referring to the exemplary embodiments of FIGS. 5A and 5B, the directing element 22 can be suitably disposed, such as to project downwardly from the underside of the cap 18 and, thus, projects downwardly within the breastshield assembly 10 when the components are fully assembled. An exterior of the media separation device 20, i.e., the outer surface 42a thereof, can be in media communication with a secondary pathway, extending from the breastshield 14 to the container 12, whereas an interior of the media separation device 20 can be in media communication with a pressure generating source, or pressure source 2 via a primary pathway. Referring to FIGS. 2B, 3, 5, and 5A, the pressure source can be placed in media communication with the interior of the media separation device 20, which can include the fluid cavity 44, to affect selective and repeatable collapse of the device 20 given a varying pressure delivered to the fluid cavity of the device from the pressure source 2.

More specifically, the pressure source may be defined by a suitable breastmilk expression system, such as a breastpump, compression system, a combination of a breastpump and compression system, or any other suitable system. The pressure source, such as pressure source 2 of FIG. 1 may include a flexible tube 1B, shown in FIG. 2B extending from the pressure source to the cap 18, where a port 18a can be provided for selectively connecting the flexible tube 1B to the cap 18. Alternatively, the pressure source can be directly connected to the media separation system of the breastshield assembly in alternative embodiments (not shown).

The pressure from the pressure source 2 is applied to the fluid cavity 44 of the media separation device through the flexible tube 1B, the port 18a, and a channel 18b in media communication with the port 18a through the cap 18. A varying pressure from the pressure source 2 can be applied to the fluid cavity 44 through the primary pathway 1A to cause the media separation device 20 to alternately collapse and then return to its original, preset geometry, or form or configuration.

As will be seen from exemplary embodiments shown in FIGS. 6A-6C, the elongate sleeve 24 has an oval-shaped axial cross-section substantially from the open end 28 to the closed end 30. The directing element 22 will also be understood to have an oval-shaped axial cross-section (see FIG. 5B), and a downwardly facing angled surface 46 which extends through a major axis X-X of the oval-shaped cross-section. Further, the channel 18b in the directing element 22 provides the necessary media communication of the fluid cavity 44 with the pressure source 2 via the primary pathway.

With this arrangement, the downwardly facing surface 46 of the directing element 22 slants away from the secondary pathway extending from the breastshield 14 to the container 12. The cap 18 has a media connection passageway, such as tubing, 1B extending from the port 18a, which is in media communication with the pressure source, to the channel 18b to apply a varying pressure to the media separation device 20. Since the downwardly facing surface 46 slants away from the secondary pathway, the milk expressed from the breast can flow freely as the media separation device 20 can collapse away from the nipple tunnel of the breastshield in the same direction as the direction of milk flow in the secondary pathway, and collapses substantially away from the secondary pathway as the pressure is applied to the fluid cavity, such that the milk flows freely to the container 12.

Figure 4:
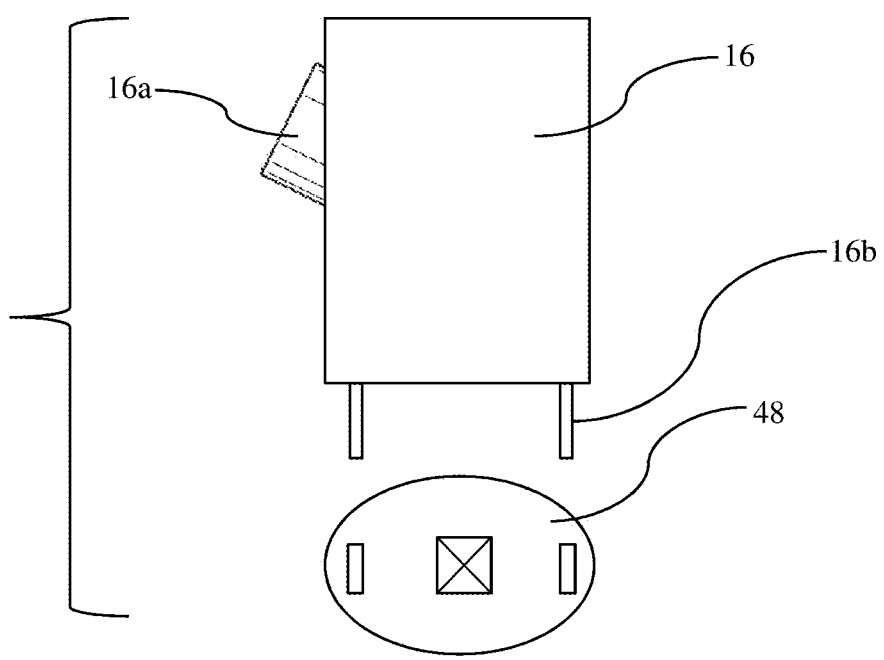
FIG. 4 is a top view of a valve system of the breastshield assembly of FIGS. 2A, 2B and 3.

Referring to the exemplary embodiments shown in FIGS. 2A, 2B and 3, the conduit system 16 in the breastmilk expression system 10 has distinct multiple interfaces. Specifically, the conduit system 16 includes an interface 16a for receiving the breastshield 14 in a suitable manner, for example in a taper fit. An interface 16b for receiving a valve 48 which, in turn, can have an interface 48a for receiving the container 12 (see FIG. 4), and an interface 16c for receiving the cap 18 in a suitable manner, for example in a snap fit. With regard to the cap 18, the directing element 22 is disposed within an oval-shaped media separation well 16d of the conduit system 16 to provide a suitable fit between components, such as a compression fit.

In particular, the media separation well 16d of the conduit system 16 serves to receive the media separation device 20. As illustrated in the exemplary embodiments FIGS. 5, 5A and 5B, the media separation device 20 is suitably disposed within the media separation well 16d of the conduit system 16 such that the lower outwardly projecting rim 40b can rest on the upper edge of the media separation well 16d, if desired. Since the media separation well 16d of the conduit system 16, the media separation device 20, and the directing element 22 on the underside of the cap 18 can all have suitable or matching geometric configurations, such as one or more of oval-shaped cross-sections or any non-circular cross-sections, for example, the components can be sized for the directing element 22 to be disposed within the media separation device 20 so that the directing element 22, the media separation device 20, and the media separation well 16d are in a snug relationship to one another. While some examples depict such matching geometric configurations as one or more of oval-shaped or non-circular cross-sections along a vertical axis, various other matching geometric configurations, e.g., shapes, for each of the media separation well 16d, the media separation device 20, and the directing element 22 may alternatively or additionally be used and still fall within the scope of the present disclosure. Exemplary embodiments herein allow the order in which these various components are assembled for use of the breastmilk expression system 10 to be reversed, if desired, although the disclosure is not limited to embodiments adapted for reversible assembly.

In other words, in an exemplary embodiment the media separation device 20 can be disposed within the media separation well 16d of the conduit system 16, following which the cap 18 can be placed on the conduit system 16 by disposing the directing element 22 on the underside of the cap 18 within the interior or fluid cavity 44 of the media separation device 20. Alternatively, the media separation device 20 can be positioned on the directing element 22 on the underside of the cap 18, following which the assembled components can be disposed within the conduit system 16 by inserting the assembled components into the media separation well 16d until there is a fitting engagement. When configured to provide for a DMS offering reversible assembly, the DMS incorporates flexibility in assembly that may benefit moms who have a preference for one assembly option over another.

As discussed above, the media separation device 20 has an elongate sleeve 24 defined by a continuous wall 26 formed of a flexible material to have an open end 28, a closed end 30, front and back wall portions 32 and 34 and opposed side wall portions 36 and 38. In an embodiment, the thicker first wall region 26a of the front and back wall portions 32 and 34 and the opposed side wall portions 36 and 38 is located generally in the area where the directing element 22 is disposed within the media separation well 16d. The thinner second wall region 26b of the front and back wall portions 32 and 34 is located remote from the thicker first wall region 26a near the open end 28 and extends about the closed end 30 of the elongate sleeve 24 with the remaining wall region 26c between the first and second wall regions 26a and 26b.

The remaining wall region 26c of the continuous wall 26 of flexible material can be formed to have a thickness which is less than the thickness of the first wall region 26a and/or greater than the thickness of the second wall region 26b. When the media separation device 20 is formed to have such thicker and thinner wall regions, the application of varying pressure to the fluid cavity 44 will cause the front and back wall portions 32 and 34 to move toward and away from each other in accordance with the system geometries, such as the preset geometry of the media separation device and the directing geometry of the directing element.

More specifically, the front and back wall portions 32 and 34 of the media separation device 20, and especially the thinner second wall region 26b located remote from the open end 28 will collapse together when subjected to a pressure and will return to their original configuration upon removing the pressure in a predictable and repeatable manner.

In another respect, the thinner second wall region 26b of the continuous wall 26 includes a first noise attenuation region which is disposed furthest from but in communication with the primary pathway. The remaining wall region 26c (between the first and second wall regions 26a and 26b) includes a second noise attenuation path which is disposed nearer to and in communication with the primary pathway. Thus, the first noise attenuation region can include the second wall region 26b which has a first pressure response and the second noise attenuation region can include the remaining wall region 26c of the continuous wall 26 which can have a second pressure response.

The media separation device 20 also advantageously includes at least one wall region of one thickness with a first pressure response, e.g., the second wall region 26b, and at least another wall region of another thickness with a second pressure response, e.g., the remaining wall region 26c where the first pressure response differs from the second pressure response for a varying pressure which is applied to both the second region 26b and the remaining wall region 26c by the pressure source.

In an embodiment, the difference in pressure response between the second wall region 26b and the remaining wall region 26c can result from the thinner nature of the second wall region 26b in relation to the thickness of the remaining wall region 26c of the continuous wall 26, or from relative geometries of the wall regions, or from a combination of thickness and geometries of the wall regions.

In prior art assemblies, a terminal end of a nipple tunnel extending from the breastshield into the conduit system is formed of a hard contact surface. During operation of a breast pump, a mother's nipple can be extended toward and come into contact with the hard contact surface at the terminal end of the nipple tunnel of prior art devices.

Figure 7A:
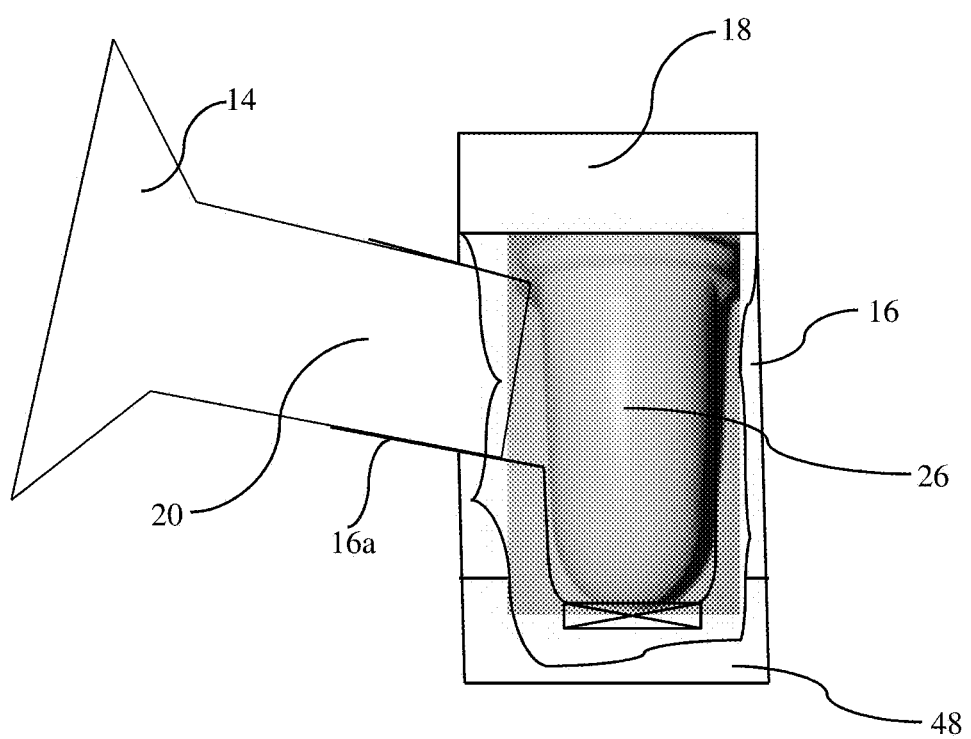
FIG. 7A illustrates an embodiment constructed in accordance with the principles herein, where a soft contact surface is provided between a breastshield and a terminal end of a nipple tunnel, the nipple tunnel extending from the breastshield and into a conduit system.

FIG. 7A illustrates an embodiment constructed in accordance with the principles herein, where a soft contact surface is provided at a terminal end 25a of a nipple tunnel 25. The soft contact surface can be formed of any suitable material, and arranged in the conduit system 16. In an embodiment, the soft contact surface can be formed by the media separation device 20.

Further, the second region 26b of the media separation device 20 can be configured, adapted, and contoured to allow for passive dropping of milk through the conduit system 16, even when the pressure source 2 is in a resting state, to facilitate the continuous passage of milk from the tunnel 25a through the media separation well 16d of the conduit system 16.

Additionally, improving the efficiency of the media separation system 1 can improve the ability of the breastmilk expression system to control the pressure that the breast is actually subjected to during operation of the system.

Moreover, operation of a system configured in accordance with the principles of the present disclosure can bring added comfort to the user. As shown in an exemplary embodiment of FIG. 7B, an exemplary media separation well 24 can be suitable disposed, such as at the terminal end 25a of a nipple tunnel 25 formed in the breastshield 14. The predictable collapse of the DMS, in conjunction with the directing element in the cap, causes the DMS to move away from the nipple of the mom, allowing for more space for the nipple to comfortably extend when subject to an applied varying pressure.

Figure 7B:
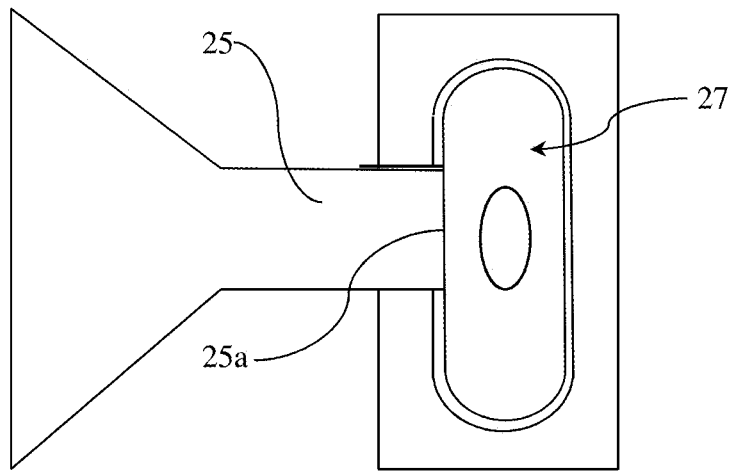
FIG. 7B illustrates an embodiment showing an exemplary media separation well, disposed at a transition point between a nipple tunnel and the media separation well.
Figure 7C:
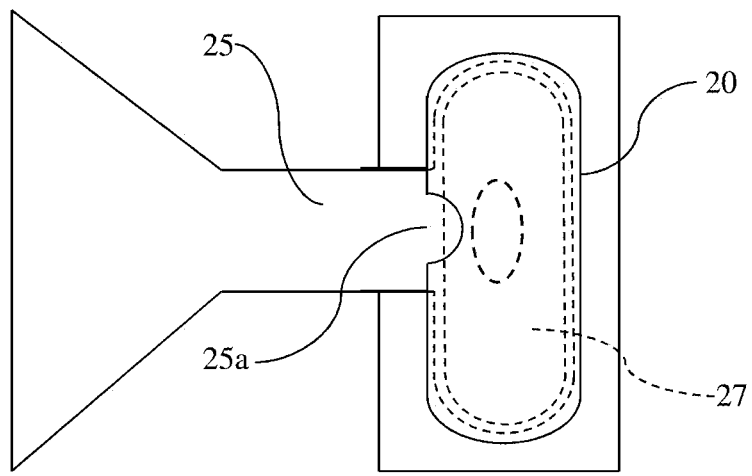
FIG. 7C illustrates an embodiment showing an exemplary media separation device forming a cushioned, soft surface within the media separation well of FIG. 7B.
Figure 7D:
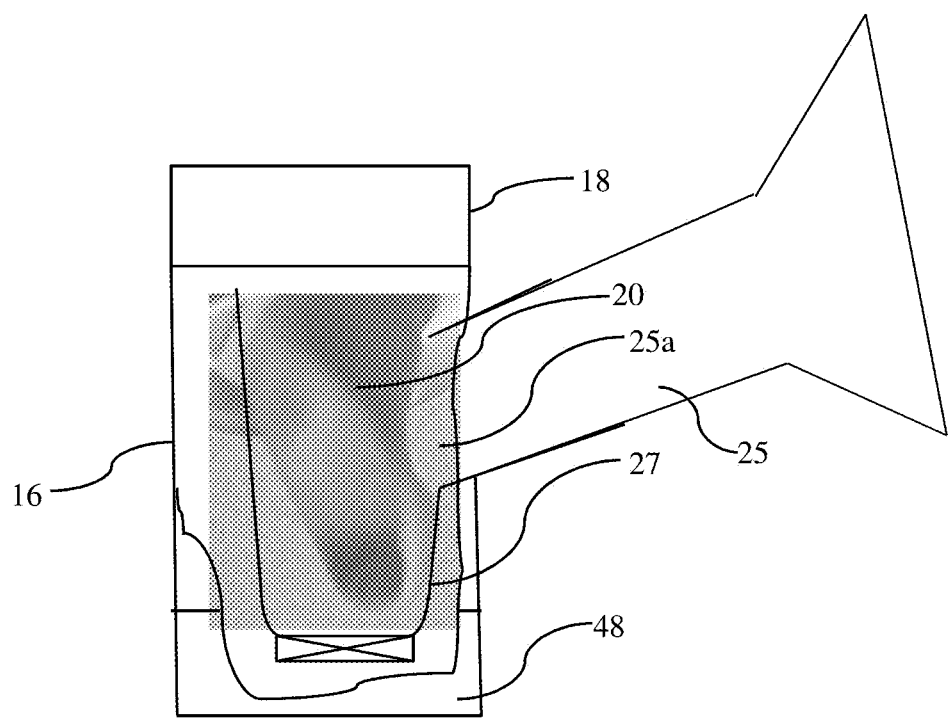
FIG. 7D illustrates the media separation device of FIG. 7C in a collapsed condition within the media separation well of FIG. 7B.

As further illustrated in the embodiment of FIGS. 7C and 7D, an exemplary media separation device 20 selectively disposed in the media separation well 24 can form a cushioned, soft surface at the end 25a of the nipple tunnel 25 of FIG. 7B. The cushioned surface can provide greater comfort for the mom if the nipple does come into contact with the DMS.

As one of ordinary skill in the art will understand, any breastmilk referred to in the foregoing disclosure, such as in reference to the breastmilk expression system, is breastmilk from a human, e.g., a human mother, and not any other mammal or species. For example, the breastmilk expression system of the present disclosure is directed to expressing breastmilk from a human mother.

While various embodiments have been described above, it will be appreciated that variations may be made thereto that are still within the scope of the appended claims.

What is claimed is:

1. A directed media separation (DMS) system in a breastshield assembly of a breastmilk expression system, a media including breastmilk, and the DMS system comprising:
   a directing element having a major axis X-X; and
   a media separation device connected to the directing element, the media separation device including:
      an inner surface defining a media cavity and adapted to be in media communication with a pressure source via a primary media pathway, the directing element downwardly extending from a center area of a cap and into a center area of the media cavity, the directing element including a channel downwardly extending from the center area of the cap into the center area of the media cavity and offset from and perpendicular to the major axis X-X; and
      an outer surface adapted to be in media communication with a secondary media pathway extending from a breastshield to a container,
   the media separation device configured with a preset geometry that affects a selective collapse of the media separation device from a directing geometry of the directing element away from the secondary media pathway in a predictable and repeatable manner relative to the directing geometry of the directing element when pressure is applied to the media separation device via the primary media pathway, and
   when the pressure is applied via the primary media pathway to the media cavity defined by the inner surface of the media separation device, the breastmilk expressed can flow freely through the secondary media pathway and into the container as the media separation device selectively collapses away from the breastshield and the secondary media pathway, and
   wherein the media separation device separates the primary media pathway from the secondary media pathway, and the media in the primary media pathway is the pressure from a vacuum source and the media in the secondary media pathway is the breastmilk.

2. The DMS system of claim 1, the media separation device formed of a flexible material capable of selectively collapsing under a varying pressure and capable of reverting to the preset geometry.

3. The DMS system of claim 1, the media separation device including an elongate sleeve defined by a continuous wall to have an open end, a closed end, front and back wall portions, and opposed side wall portions.

4. The DMS system of claim 3, including one or more outwardly projecting rims where the open end of the sleeve engages the directing element.

5. The DMS system of claim 1, the media separation device including at least one first wall region configured to generate a first pressure response and at least one second wall region configured to generate a second pressure response, the first pressure response of the at least one first wall region differing from the second pressure response of the at least one second wall region when a given pressure is applied to the DMS system.

6. The DMS system of claim 3, the media separation device having i) the front and back wall portions and opposed side wall portions each including a first wall region of a first thickness extending from the open end toward the closed end of the elongate sleeve, ii) the front and back wall portions each including a second wall region of a second thickness extending from the closed end toward the open end of the elongate sleeve, and iii) a remaining wall region between the first wall region and the second wall region of the media separation device having a third thickness, wherein the third thickness is further defined by at least one of less than the first thickness and greater than the second thickness.

7. The DMS system of claim 6, the first thickness of the first wall region of each of the opposed side wall portions being chevron-shaped and the second thickness of the second wall region of each of the front and back wall portions being inverted U-shaped.

8. The DMS system of claim 3, the media separation device configured to allow portions of the continuous wall, to selectively collapse, the continuous wall having an outer surface and an inner surface defining a fluid cavity, a first wall region including a projection of the inner surface of the continuous wall into the fluid cavity and a second wall region including a recess in the outer surface of the continuous wall.

9. The DMS system of claim 3, the directing element projecting downwardly into the elongate sleeve, an outer surface of the media separation device in communication with the secondary pathway from the breastshield to the container, the elongate sleeve of the media separation device configured to undergo a negative pressure change from varying pressure applied via the primary pathway through the directing element and to the media separation device.

10. The DMS system of claim 9, the directing element having an oval-shaped axial cross-section, a downwardly facing angled surface through the major axis X-X of the oval-shaped axial cross-section, and the channel configured to enable selective communication with an interior of the media separation device.

11. The DMS system of claim 10, further including a conduit system having multiple interfaces, including an interface for receiving the breastshield, an interface for receiving the cap, the downwardly projecting directing element disposed within the cap, and an interface for receiving the container, the conduit system further including a media separation well configured to selectively receive the media separation device.

12. A media separation system in a breastshield assembly of a breastmilk expression system, a media including breastmilk and the media separation system comprising:
an elongate sleeve adapted to be coupled to a directing element having a major axis X-X and defined by a continuous wall formed of a flexible material to have an open end, a closed end, front and back wall portions, opposed side wall portions, an inner surface defining a media cavity and adapted to be in media communication with a pressure source via a primary media pathway, the directing element downwardly extending into a center area of the media cavity and having an oval-shaped axial cross-section, the directing element including a channel downwardly extending from the center area of the cap into the center area of the media cavity and offset from and perpendicular to the major axis X-X, and an outer surface adapted to be in media communication with a secondary media pathway extending from a breastshield to a container;
the front and back wall portions and the opposed side wall portions each including a first wall region of a first thickness extending from the open end toward the closed end of the elongate sleeve, and the front and back wall portions each including a second wall region of a second thickness extending from the closed end toward the open end of the elongate sleeve;
a remaining wall region of the continuous wall having a third thickness that can vary to be at least one of less than the first thickness of the first wall region and greater than the second thickness of the second wall region,
the elongate sleeve selectively collapses from a directing geometry of the directing element away from the secondary media pathway in a predictable and repeatable manner relative to the directing geometry of the directing element, and
as pressure is applied to the media cavity defined by the inner surface, breastmilk expressed can flow freely through the secondary media pathway to the container as a media separation device selectively collapses away from the breastshield and the secondary media pathway, the secondary media pathway in media communication with the outer surface, and
wherein the media separation device separates the primary media pathway from the secondary media pathway, and the media in the primary media pathway is the pressure from a vacuum source and the media in the secondary media pathway is the breastmilk.

13. The media separation system of claim 12, the elongate sleeve including an outwardly projecting rim, the open end of the elongate sleeve configured to removably engage the directing element.

14. The media separation system of claim 12, the first thickness of the first wall region of each of the opposed side wall portions being chevron-shaped.

15. The media separation system of claim 12, the second thickness of the second wall region of each of the front and back wall portions being inverted U-shaped.

16. The media separation system of claim 15, the second thickness of the second wall region of each of the front and back wall portions extending about the closed end.

17. The media separation system of claim 12, the continuous wall having an outer surface and an inner surface, the inner surface defining a fluid cavity of the elongate sleeve.

18. The media separation system of claim 17, the first wall region having a projection relative to a remainder of the inner surface of the continuous wall.

19. The media separation system of claim 17, the second wall region having a recess relative to a remainder of the outer surface of the continuous wall.

20. The media separation system of claim 12, the elongate sleeve having an oval-shaped axial cross-section extending substantially from the open end to the closed end.

21. The media separation system of claim 12, the first wall region configured to generate a first pressure response and the second wall region configured to generate a second pressure response differing from the first pressure response of the first wall region when a given pressure is applied to the media separation system.

22. The media separation system of claim 13, in combination with the breastmilk expression system including the container, the breastshield, a conduit system, and a cap, the directing element projecting downward from the cap, an exterior of the media separation device in communication with the secondary pathway from the breastshield to the container, and an interior of the media separation device in communication with the primary pathway of a pressure source to apply a varying pressure to the media separation system.

23. The media separation system of claim 22, the conduit system having a media separation well of oval-shaped cross-section for receiving the media separation device.

24. The media separation system of claim 22, the directing element having the oval-shaped axial cross-section, an angled surface through the major axis X-X of the oval-shaped axial cross-section opposite to the cap, and the channel for communication of the interior of the media separation device with the pressure source.

25. The media separation system of claim 24, the angled surface of the directing element slanting downwardly away from the secondary pathway extending from the breastshield to the container.

26. The media separation system of claim 24, the cap having the primary passageway extending from a port in media communication with the pressure source to the channel of the directing element.

27. A media separation device in a breastshield of a breastmilk expression system, a media including breastmilk and the media separation device comprising:
at least one wall region of one thickness with a first pressure response and at least another wall region of another thickness with a second pressure response; and an elongate sleeve defined by a continuous wall to have an open end, a closed end, front and back wall portions, and opposed side wall portions, and the continuous wall having an outer surface and an inner surface defining a media cavity, a first wall region including a projection of the inner surface of the continuous wall into a fluid cavity and a second wall region including a recess in the outer surface of the continuous wall, the at least one wall region having an inner surface and an outer surface, the inner surface defining the media cavity and adapted to be in media communication with a pressure source via a primary media pathway, and the outer surface adapted to be in media communication with a secondary media pathway extending from the breastshield to a container;

the at least one wall region and the at least another wall region adapted to be connected to a directing element downwardly extending from a center of a cap into a center area of the media cavity, the directing element having a major axis X-X and including a channel downwardly extending from the center area of the cap into the center area of the media cavity and offset from and perpendicular to the major axis X-X;

the first pressure response differing from the second pressure response for a given pressure applied to both of the at least one wall region and the at least another wall region, where, as pressure is applied to the media cavity defined by the inner surface of the media separation device, the breastmilk expressed can flow freely through the secondary media pathway to the container as the media separation device selectively collapses away from the breastshield and the secondary media pathway, the secondary media pathway in media communication with the outer surface of the media separation device, wherein the media separation device separates the primary media pathway from the secondary media pathway, and the media in the primary media pathway is the pressure from a vacuum source and the media in the secondary media pathway is the breastmilk.

28. The media separation device of claim 27, wherein the first wall region is associated with the front and back wall portions and opposed side wall portions, and the second wall region, associated with the front and back wall portions, extending about the closed end of the continuous wall, the first wall region of the continuous wall extending from the open end toward the closed end of the elongate sleeve and the second wall region of the continuous wall extending from the closed end toward the open end of the elongate sleeve, and a remaining wall region between the first wall region and the second wall region, where the second wall region comprises the wall region having the first pressure response and the remaining wall region comprises the wall region having the second pressure response.

29. The media separation device of claim 28, wherein the remaining wall region is thicker than the second wall region.

30. A breastmilk expression system comprising a media separation device, a container, a breastshield, a conduit system, and a cap, a directing element projecting downward from a center of the cap and into a center area of a media cavity of the media separation device, the directing element having a major axis X-X and a channel downwardly extending from the center area of the cap into the center area of the media cavity and offset from and perpendicular to the major axis X-X, an exterior of the media separation device in communication with a secondary pathway from the breastshield to the container, and an interior of the media separation device in communication with a primary pathway of a pressure source to apply a varying pressure to the breastmilk expression system, the media separation device configured with a preset geometry that affects a selective collapse of the media separation device from a directing geometry of the directing element away from the secondary media pathway from the breastshield to the container in a predictable and repeatable manner relative to the directing geometry of the directing element when pressure is applied to the media separation device via the primary media pathway, and as the pressure is applied to the media cavity defined by the inner surface of the media separation device, breastmilk expressed can flow freely through the secondary media pathway to the container as the media separation device selectively collapses away from the breastshield and the secondary media pathway, the secondary media pathway in media communication with the outer surface of the media separation device, and wherein the media separation device separates the primary media pathway from the secondary media pathway, and a media in the primary media pathway is pressure from a vacuum source and the media in the secondary media pathway is the breastmilk.

* * * * *